United States Patent
Liang (10) Patent No.: US 12,038,627 B2
(45) Date of Patent: Jul. 16, 2024

(54) METHODS AND SYSTEMS OF REFRACTION AUTOMATION FOR PRESCRIBING EYEGLASSES

(71) Applicant: PERFECT VISION TECHNOLOGY (HK) LTD., Tsuen Wan (HK)

(72) Inventor: Junzhong Liang, Fremont, CA (US)

(73) Assignee: PERFECT VISION TECHNOLOGY (HK) LTD., Tsuen Wan (HK)

(*) Notice: Subject to any disclaimer, the term of this patent is extended or adjusted under 35 U.S.C. 154(b) by 933 days.

(21) Appl. No.: 17/062,350

(22) Filed: Oct. 2, 2020

(65) Prior Publication Data

US 2021/0018764 A1 Jan. 21, 2021

Related U.S. Application Data

(63) Continuation of application No. PCT/US2018/041622, filed on Jul. 11, 2018.
(Continued)

(51) Int. Cl.
G02C 7/02 (2006.01)
A61B 3/10 (2006.01)
A61B 3/103 (2006.01)

(52) U.S. Cl.
CPC ............ *G02C 7/027* (2013.01); *A61B 3/1015* (2013.01); *A61B 3/103* (2013.01); *A61B 3/1005* (2013.01)

(58) Field of Classification Search
CPC ........ G02C 7/027; A61B 3/1015; A61B 3/103
(Continued)

(56) References Cited

U.S. PATENT DOCUMENTS 5,777,719 A * 7/1998 Williams ................. A61B 3/14
351/200
5,914,772 A 6/1999 Dyer
(Continued)

FOREIGN PATENT DOCUMENTS

JP 2003042905 A 2/2003
JP 2003107342 A * 4/2023 ............... G02C 7/02
WO WO-2014085352 A1 * 6/2014 ........... A61B 3/0025

OTHER PUBLICATIONS

International Search Report dated Dec. 10, 2018 for PCT Patent Application No. PCT/US2018/041622.

*Primary Examiner* — James R Greece
(74) *Attorney, Agent, or Firm* — MLO, a professional corp.

(57) ABSTRACT

Methods and systems for determining a refractive correction for eyeglasses involve obtaining an objective measurement of a wave aberration. The objective measurement includes an objective spherical power (SPH_o), an objective cylinder power (CYL_o), an objective cylinder axis (AXIS_o), and other residual aberrations; and uses objective vision optimization to achieve a best image quality for the eye from the residual aberrations. A prescription cylinder power (CYL_p), is determined using a software module, where an absolute value of CYL_p is less than an absolute value of CYL_o and achieves an acuity of at least 20/20. A prescription spherical power (SPH_s) is determined subjectively by dialing into a phoropter module a cylinder correction according to the prescription cylinder power (CYL_p) from the software module and the objective cylinder axis (AXIS_o) according to the objective aberrometer module. A prescription for an ophthalmic lens of the eyeglasses is generated that includes SPH_s, CYL_p and AXIS_o.

8 Claims, 5 Drawing Sheets

Related U.S. Application Data

(60) Provisional application No. 62/653,700, filed on Apr. 6, 2018.

(58) Field of Classification Search
USPC .................................................. 351/159.75
See application file for complete search history.

(56) References Cited

U.S. PATENT DOCUMENTS

| | | | |
|---|---|---|---|
| 2010/0110379 A1 | 5/2010 | Zhou et al. | |
| 2016/0242641 A1 | 8/2016 | Liang | |
| 2017/0265738 A1* | 9/2017 | Keita | A61B 3/103 |
| 2017/0329154 A1 | 11/2017 | Liang | |

* cited by examiner

METHODS AND SYSTEMS OF REFRACTION AUTOMATION FOR PRESCRIBING EYEGLASSES

RELATED APPLICATIONS

This application is a continuation of International Application No. PCT/US2018/041622 filed on Jul. 11, 2018 and entitled "Methods and Systems of Refraction Automation for Prescribing Eyeglasses"; which claims priority to U.S. Provisional Patent Application No. 62/653,700 filed on Apr. 6, 2018 and entitled "Methods and Systems of Refraction Automation for Prescribing Eyeglasses," both of which are hereby incorporated by reference for all purposes.

BACKGROUND

Conventional refraction processes rely on the experience and skill's of an individual eye care professional (e.g., an optometrist or optician) to set the starting and ending points of a spherical power, a cylinder power, and a cylinder axis for an eyeglass prescription.

Figure 1:
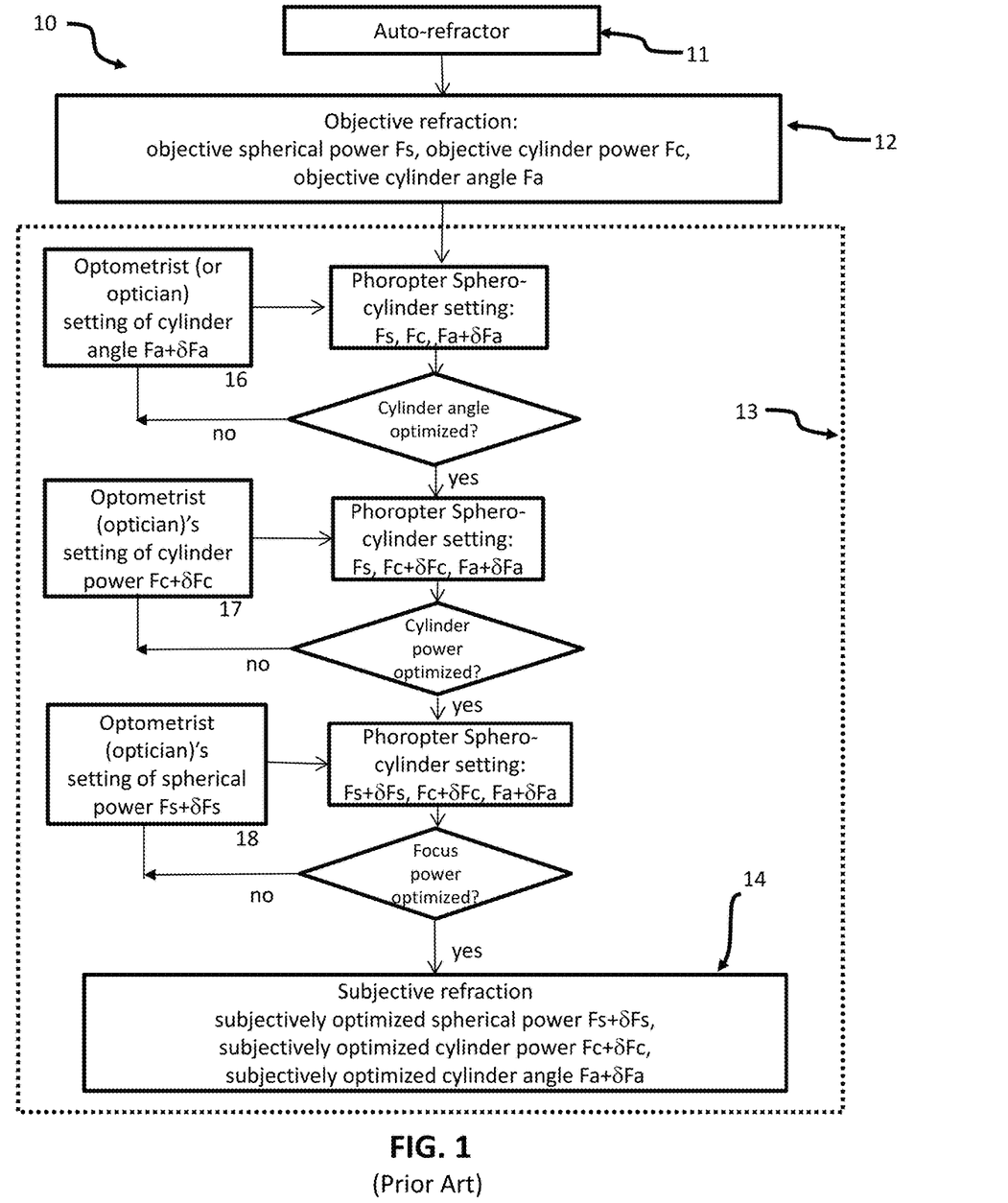
FIG. 1 shows a block diagram of a conventional refraction process.

A block diagram 10 representing a conventional refraction process is shown in FIG. 1. First, an autorefractor 11 is typically used to take an objective measurement of an eye's refractive errors and provide a rough objective prescription in objective refraction step 12, where the objective prescription includes an objective spherical power $F_s$, an objective cylinder power $F_c$ and an objective cylinder angle $F_a$. Second, an eye care professional determines a rough spherical correction in a phoropter 13, and then administrates a subjective optimization of spherical power, cylinder power and cylinder angle based on the objective prescription from step 12. The subjective optimization is based on the experience and skill of the optometrist or optician, and on subjective feedback of the tested subject (i.e., the patient).

Steps 16, 17 and 18 are part of the subjective refraction performed using the phoropter 13. In step 16, the cylinder angle $F_a$ is subjectively optimized by letting the tested subject first see an astigmatism chart and then an acuity chart afterwards. The eye care professional will set and modify the cylinder angle by an amount $\delta F_a$ based on the objective prescription of step 12 as well as feedback of the tested subject. In step 17, the cylinder power $F_c$ is subjectively optimized by having the tested subject view an acuity chart, and an eye care professional will set and modify the cylinder power by an amount $\delta F_c$ based on the objective prescription as well as feedback of the tested subject. In step 18, the spherical power is subjectively optimized by letting the tested subject see an acuity chart, and an eye care professional will set and modify the spherical power $F_s$ by an amount $\delta F_s$ based on feedback of the tested subject. The same process of steps 16, 17 and 18 are repeated for the other eye of the tested subject. In subjective refraction step 14, a final prescription of the eyeglasses is determined for each eye using the subjectively optimized spherical power $F_s+\delta F_s$ of step 18, the subjectively optimized cylinder power $F_c+\delta F_c$ of step 17, and the subjectively optimized cylinder angle $F_a+\delta F_a$ of step 16.

This conventional approach is subjective and has at least three drawbacks. First, the process relies on "human intelligence" or the experience of the eye care professional, and therefore it cannot be standardized because each eye care professional has his/her own individual experience. Second, if a patient does not like the new eyeglasses, the eye care professional makes personal adjustments to the new prescription, and new eyeglasses are made for the patient. Remaking new eyeglasses is common today, and may take a few iterations until a patient finally accepts a new pair of eyeglasses. Third, a pair of new eyeglasses may take 1 to 2 weeks for the patient to get used to, and the individual's experience varies from person to person. Adjusting to wearing the new eyeglasses can sometimes be a painful process for the patient, where a significant portion of new eyeglasses purchased are abandoned because the patient (i.e., consumer) can never get used to them.

Consequently, although many configurations and methods for vision correction are known in the art, these conventional methods and systems suffer from one or more disadvantages.

SUMMARY

In some embodiments, a method for determining a refractive correction for eyeglasses includes obtaining an objective measurement of a wave aberration of an eye of a patient, determining a prescription cylinder power (CYL_p), determining a prescription spherical power (SPH_s), and generating a prescription for an ophthalmic lens of the eyeglasses. The obtaining an objective measurement of a wave aberration of an eye of a patient involves using an objective aberrometer module. The objective measurement includes an objective spherical power (SPH_o), an objective cylinder power (CYL_o), an objective cylinder axis (AXIS_o), and residual aberrations. The objective measurement does not involve responses from the patient, and the objective measurement uses objective vision optimization to achieve a best image quality for the eye. A software module is used to determine the prescription cylinder power (CYL_p), where an absolute value of the prescription cylinder power is less than an absolute value of the objective cylinder power (CYL_o), and achieves an acuity of at least 20/20. The prescription spherical power (SPH_s) is determined through a subjective refraction involving subjective responses of the patient to a plurality of spherical powers. The subjective refraction involves using a phoropter module having a plurality of spherical lenses and cylindrical lenses and dialing into the phoropter module: i) a cylinder correction according to the prescription cylinder power (CYL_p) from the software module, and ii) the objective cylinder axis (AXIS_o) according to the objective aberrometer module. The generated prescription includes: a) the prescription spherical power (SPH_s) that is determined through the subjective refraction, b) the prescription cylinder power (CYL_p) that is determined by the software module, and c) the objective cylinder axis (AXIS_o) that is determined from the objective measurement of the wave aberration.

In some embodiments, a system for determining a refractive correction for eyeglasses includes an objective aberrometer module, a software module, and a phoropter module. The objective aberrometer module is configured to obtain an objective measurement of a wave aberration of an eye of a patient. The objective measurement includes an objective spherical power (SPH_o), an objective cylinder power (CYL_o), an objective cylinder axis (AXIS_o), and residual aberrations. The objective measurement does not involve responses from the patient, and the objective measurement uses objective vision optimization to achieve a best image quality for the eye. The software module is configured to determine a prescription cylinder power (CYL_p), where an absolute value of the prescription cylinder power is less than an absolute value of the objective cylinder power (CYL_o) and achieves an acuity of at least 20/20. The phoropter module has a plurality of spherical lenses and cylindrical lenses or has one or more electrically-controlled lenses that is/are capable of achieving different sphero-cylinder corrections, where the phoropter module is used for determining a prescription spherical power of the eye through a subjective refraction involving subjective responses of the patient to a plurality of spherical powers. The phoropter module is configured to dial in, to the cylindrical lenses: i) a cylinder correction according to the prescription cylinder power (CYL_p) from the software module, and ii) the objective cylinder axis (AXIS_o) according to the objective aberrometer module. The prescription for the ophthalmic lens of the eyeglasses includes: a) the prescription spherical power (SPH_s) that is determined through the subjective refraction, b) the prescription cylinder power (CYL_p) that is determined by the software module, and c) the objective cylinder axis (AXIS_o) that is determined from the objective measurement of the wave aberration.

DETAILED DESCRIPTION

Methods and systems for automated refraction for eyeglasses are disclosed such that patients are provided with a pair of eyeglasses that not only provides clear, vision but also provides comfortable viewing. A prescription for eyeglasses is generated such that a cylinder power in the prescription is used to achieve 20/20 acuity, where the prescription cylinder power may be less (in absolute value) than what would be required according to an objective aberrometer measurement. The prescription cylinder power is determined by adjusting the objectively-measured cylinder power, consequently enabling a more acceptable image distortion in a trade-off from better acuity (e.g., 20/10 acuity that would be achieved by using the objectively-measured cylinder power). The automated refraction of human eyes in the present methods can be delegated to technicians, rather than relying on the expertise of an optician or optometrist. This automation is achieved by starting with objective measurements for cylinder power, cylinder axis and spherical power, using a software module to adjust the objectively-measured cylinder power, and then having the patient decide only the spherical power in a subjective refraction to achieve a prescription that is acceptable for the patient in not only vision correction but providing viewing comfort.

Lenses of eyeglasses are typically placed about 12 mm in front of the corneas of human eyes while node points of eyes are usually a few millimeters behind corneas of eyes in human anatomy. Because of the distance from the lens to the node point of the eye, a cylinder correction from eyeglasses, which is required for improving retinal image quality, can also cause image distortion. This image distortion can be problematic for some people in the adoption of new eyeglasses by causing, for example, headaches, or eye strain.

Thus, the best refraction solution for a pair of eyeglasses is not necessarily an eyeglass that provides the best retinal image quality for that individual. To many patients, a balanced vision for both an acceptable retinal image quality and acceptable distortion will be more appropriate.

The refraction corrections for eyeglasses are typically represented by a spherical power and an astigmatism. In this disclosure, spherical power ("SPH" in the present embodiments) may also be referred to as a focus error or focus power. The astigmatism (AST) includes a cylinder power ("CYL" in the present embodiments) and a cylinder axis ("AXIS" in the present embodiments), where the cylinder axis may also be referred to as a cylinder angle.

Wavefront aberrometers are known to provide objective measurements of all the aberrations in human eyes. An eye's aberrations cause retinal image blur and degrade visual acuity. Refractive correction for eyeglasses involves the determination of the aberrations in the eye that can be incorporated into corrective eyeglasses.

After obtaining an eye's wave aberrations, which is a 2D function $W(x,y)$ at the pupil plane, one can determine:
1) An objective refractive correction for eyeglasses that can be expressed as an objective spherical power ("SPH_o"), an objective cylinder power ("CYL_o"), and an objective cylinder axis ("AXIS_o").
2) The residual aberrations $R(x,y)$ in the eye when SPH_o and astigmatism (CYL_o, AXIS_o) are completely corrected, i.e., $R(x,y)=W(x,y)-SPH-CYL$ (power, AXIS). Residual aberrations may include coma, spherical aberration, and a host of other aberrations (commonly expressed by Zernike aberrations).
3) Calculated retinal images of an acuity chart from the residual aberrations, from which the potential for the best corrected acuity can be estimated.

Figure 2A:
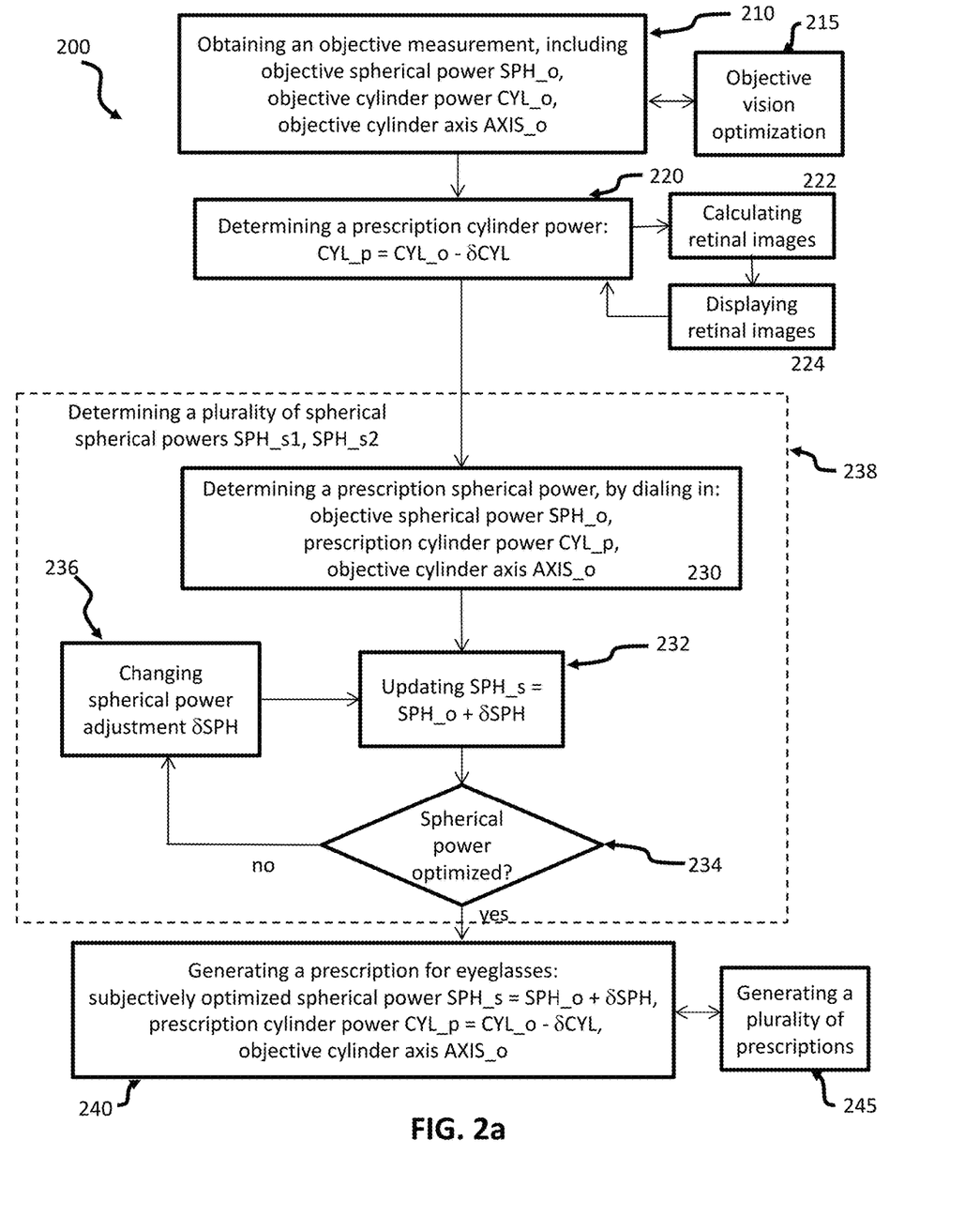
FIG. 2a shows a flow chart for a method of refraction automation, in accordance with some embodiments.

FIG. 2a is a flowchart of a method 200 for determining refractive corrections (i.e., prescriptions) for eyeglasses, in accordance with some embodiments. The method 200 also represents information processing methods for a refraction system that determines a refractive correction for eyeglasses.

Step 210 of the method 200 for determining a refractive correction for eyeglasses involves obtaining an objective measurement of wave aberration of an eye of a patient using an objective aberrometer module. In some embodiments, the objective aberrometer module uses a lens array or a Hartmann-Shack sensor for the measurement of the eye's wave aberration. Objective aberrometers used in the present embodiments can also be constructed in other principles and device configurations such as laser ray tracing, spatially resolved refractometer, Talbot-Moire interferometry, skiascopic phase difference, Tscherning principle, etc.

The objective wavefront measurement includes all the aberrations in the eye. That is, the objective measurement includes an objective spherical power (SPH_o), an objective cylinder power (CYL_o), an objective cylinder axis (AXIS_o), and residual aberrations. An objective prescription (i.e., vision correction determined for typical eyeglasses by objective measurements) is determined from the wavefront measurement, including an objective spherical power SPH_o, an objective cylinder power CYL_o and an objective cylinder axis AXIS_o. The objective prescription is targeted to provide the best image quality (i.e., the best retinal image quality possible) for the eye from the measured wave aberration in the eye. The objective measurement uses objective vision optimization to achieve a best image quality for the eye from the residual aberrations.

Determining the objective prescription from the eye's aberration is performed objectively; that is, the objective measurement does not involve responses from the patient. In one embodiment, the objective corrections of SPH_o, CYL_o, and AXIS_o are determined by minimizing the residual RMS (Root Mean Square) wavefront error from the objective measurement of a wave aberration of an eye of a patient (W(x,y)). In another embodiment, the objective corrections of SPH_o, CYL_o, and AXIS_o are determined through objective vision optimization 215 to achieve a best image quality possible. This objective vision optimization 215 can be achieved by 1) numerically varying all three parameters of SPH_o, CYL_o, and AXIS_o in a plurality of combinations, 2) calculating retinal image quality objectively for each combination in the plurality of the combinations, and 3) determining a combination of SPH_o, CYL_o, and AXIS_o to achieve the best image quality (i.e., the best objective retinal image quality). The optimization is performed in an automated manner, where the many combinations of SPH_o, CYL_o, and AXIS_o can be computed quickly by a computer processor.

In one embodiment, objective retinal image quality in step 215 is measured by one or more of the following parameters: Strehl ratio (peak intensity) of a point-spread function, the half-height width of a point-spread function, modulation transfer function at a spatial frequency. For example, certain spatial frequencies may be used such as 30 cycles/degree (fundamental frequency for 20/20), 60 cycles/degree (fundamental frequency for 20/20), or their variations.

In yet another embodiment, the objective corrections of SPH_o, CYL_o, and AXIS_o are determined through objective vision optimization 215 that is performed through cloud computing.

The cylinder power CYL_o in wave aberrometers is normally measured in an increment finer than 0.25 D; that is, the cylinder power measurements have a resolution of finer than 0.25 D. Because an aberrometer is very precise, the objective cylinder power is typically in an increment of 0.01 D (e.g., measurement intervals of 2.00, 2.01, 2.02, 2.03 etc.). However, other increments for the objective cylinder power are possible, such as 0.05 D (e.g., measurement intervals of 2.00, 2.05, 2.10, 2.15, 2.20, etc.).

Step 220 involves determining a prescription cylinder power CYL_p using a software module. The software module determines the prescription cylinder power such that an absolute value of CYL_p is less than an absolute value of the objective cylinder power (CYL_o), to achieve reduced image distortion of toric eyeglasses but that achieves an acuity of at least 20/20 under the correction. In other words, the software module may choose a cylinder power for the prescription that is less than what is needed to achieve a best vision condition (e.g., 20/10, 20/12) while still ensuring that the corrected eye will achieve an acuity of at least 20/20. For example, the absolute value of the prescription cylinder power (CYL_p) ranges between a) the objective cylinder power (CYL_o) rounded down to a nearest 0.25 D, and b) the objective cylinder power reduced (CYL_o) by 0.75 D in absolute value. The exact amount of δCYL will differ from eye to eye. The resulting prescription cylinder power is |CYL_p|=CYL_o−δCYL. In other words, the prescription cylinder power can be up to 0.75 D less than the absolute value of the objective cylinder power, or can remain as much as the closest, lower 0.25 D increment of the objective cylinder power. For example, if CYL_o is −1.19 D, then CYL_p may be chosen to be anywhere in the range of −0.44 D to −1.00 D. The absolute value of −0.44 D is the absolute value of −1.19 minus |δCYL|=0.75, and −1.00 D is |−1.19| rounded down to the nearest 0.25. In general, CYL_p is usually rounded to its nearest 0.25 D to match to the standard power increment for stock lenses. Although negative cylinder powers are used in this disclosure as examples, it shall be understood by those of ordinary skill in the art that examples for cylinder power in positive convention can also be similarly utilized in the scope of this disclosure.

In one embodiment, the reduction δCYL from the objective cylinder power (CYL_o) to the prescription cylinder power (CYL_p) is determined by calculating retinal images in step 222 for a plurality of cylinder power values including (CYL_o) under the same objective cylinder angle (AXIS_o). Visual acuity under the prescription cylinder power (CYL_p) and the objective cylinder axis (AXIS_o) is estimated to be (i.e., targeted at) 20/20 or better from the calculated retinal images. Because the prescription cylinder power (CYL_p) is less than the CYL_o, the image distortion caused by the prescription cylinder power (CYL_p) will be reduced.

Figure 2B:
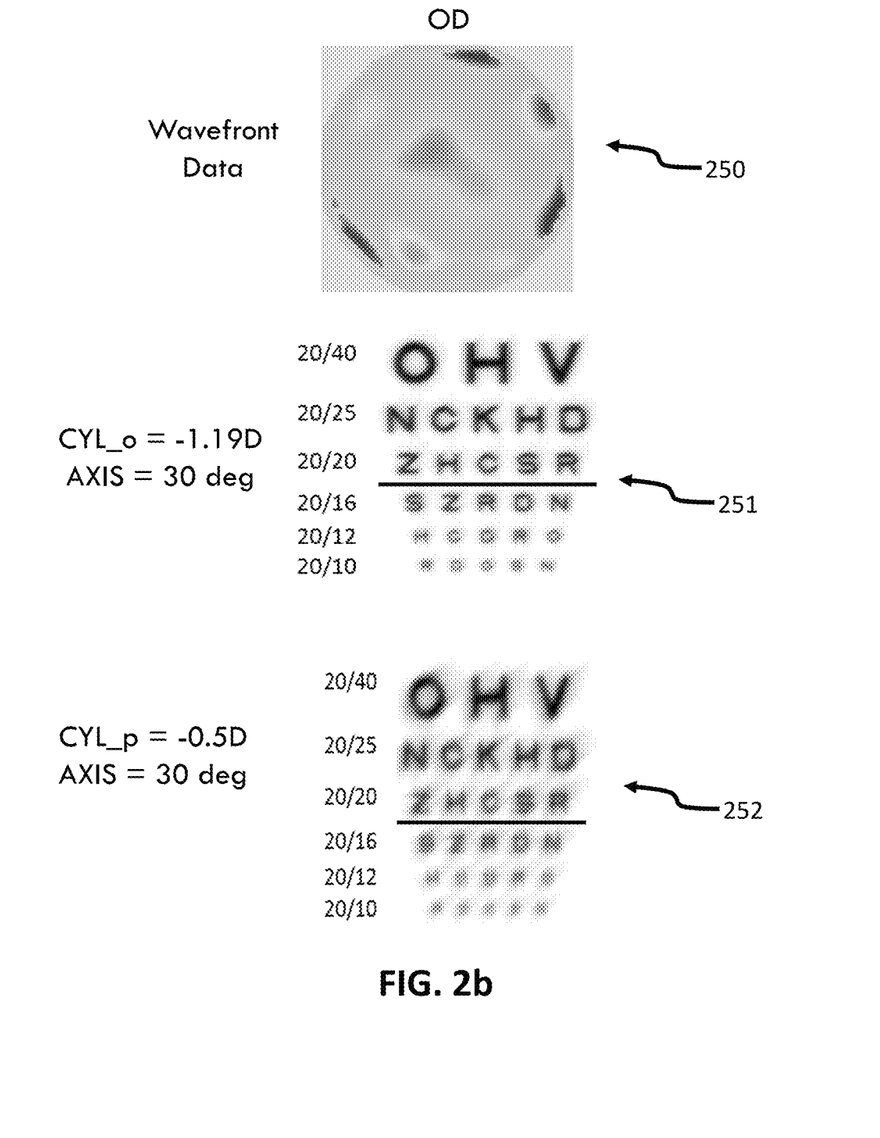
FIG. 2b shows an example for determining prescription cylinder power for eyeglasses, in accordance with some embodiments.

FIG. 2b shows an example of wavefront measurements and calculated retinal images for a tested eye for steps 220, 222 and 224. Wavefront aberration in the human eye in this example is determined with a Hartmann-Shack sensor, and the calculated objective refraction is SPH_o=−0.65 D, CYL_o=−1.19 D, AXIS_o=30 degree (deg). When the objective prescription is corrected for the tested eye, residual wavefront distribution is calculated and shown in data 250 (top row in FIG. 2b). From the residual wave aberration data 250, the following values are calculated: 1) the point-spread function of the eye, and 2) the retinal image of an acuity chart 251 (middle row in FIG. 2b) by convolving the calculated point-spread function with an acuity chart. The acuity chart image in 251 consists of letters at different sizes for 20/10 (bottom row, and the smallest in size), 20/12, 20/16, 20/20, 20/25, 20/40 (top row, and the largest in size). It is seen that, when the objective refraction is completely corrected, the eye has the potential to see 20/10 or 20/12 based on the estimated retinal image quality. However, real subjective acuity of an eye also depends on performance of eye's retina.

As an example, a toric lens with the cylinder power of −1.19 D at 30 deg may be prescribed to provide the eye with the clearest vision possible (20/10 or 20/12 vision) with eyeglasses. However, because the lens is about 16 mm in front of the nodal point of anatomical eye, it is possible the toric lenses with cylinder power of −1.19 D can cause image distortion at the same time, which may not be acceptable to the tested eye.

To address the issue of possible distortion in the −1.19 D/30 deg toric lens example, in one embodiment, the software module in the present disclosure determines a prescription cylinder power of −0.5 D, which is much smaller in cylinder power in magnitude than −1.19 D, to provide reduced image quality and reduced image distortion at the same time. When the new cylinder prescription of CYL_p=−0.5 D and Axis_o=30 deg is corrected, a new residual aberration is calculated, which includes the aberrations in data 250 plus the uncorrected cylinder power of −0.69 D at 30 deg. From the new residual wave aberration (not shown), the following are calculated: 1) a new point-spread function of the eye, 2) the retinal image of an acuity chart 252 (bottom row in FIG. 2b), by convolving the calculated point-spread function with the same acuity chart. It is seen that when the prescription cylinder power (CYL_p=−0.5 D) instead of the objective cylinder power (CYL_o=−1.19 D) is corrected, the retinal image of the eye 252 is blurred in comparison to that in acuity chart retinal image 251, but still has the potential to see 20/20. This fulfills the requirement to find a prescription cylinder power (CYL_p) that is less than the objective cylinder power (CYL_o) for reduced image distortion, while the correction under the prescription cylinder power (CYL_p) still ensures achieving visual acuity of 20/20.

In one embodiment, the acuity chart in the calculation includes letters for 20/20, 20/25, 20/30, 20/40, with the finest acuity of 20/20. In another embodiment, the acuity chart includes letters for 20/10, 20/12, 20/16, 20/20, 20/25, 20/30, 20/40, and possibly higher with the finest acuity of 20/10.

In yet another embodiment, the method 200 further comprises step 224 of displaying (i.e., to present for viewing to the operator and patient) the calculated retinal images for two cylinder corrections (e.g., images 251 and 252 in FIG. 2b). The two cylinder corrections displayed are the cylinder powers of CYL_o and CYL_p with the same cylinder axis of AXIS_o. In other words, the cylinder corrections that are displayed are a) CYL_o with AXIS_o for the best image quality, and b) CYL_p with AXIS_o for balanced vision retinal image quality and reduced image distortion.

Figure 2C:
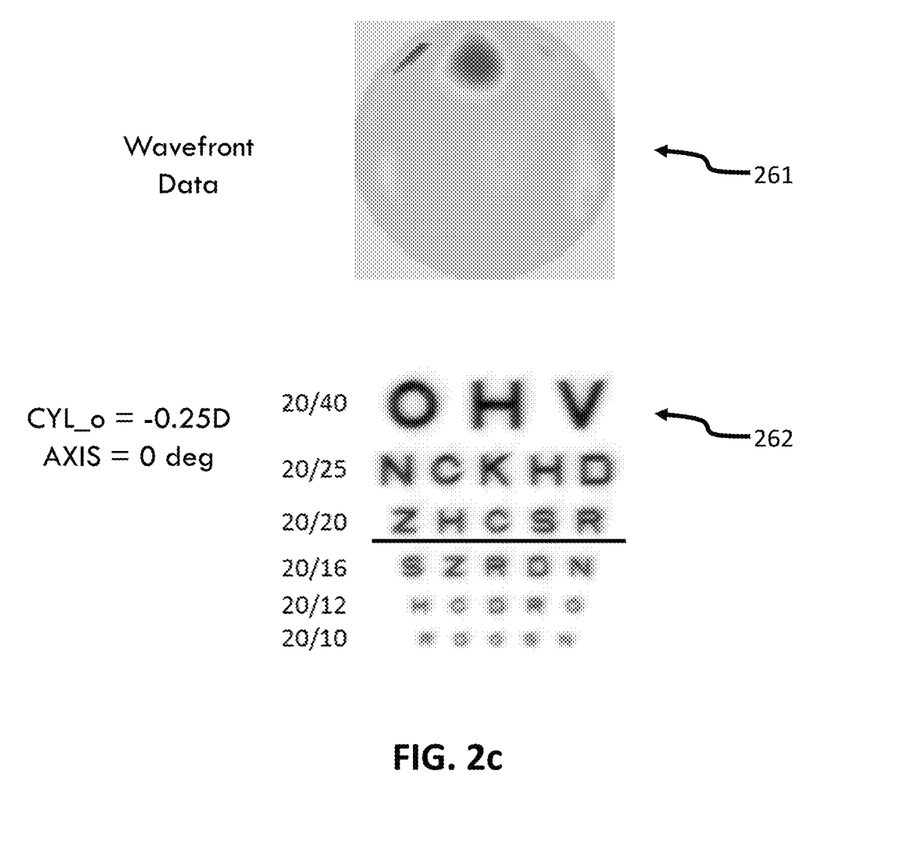
FIG. 2c shows an example of vision diagnosis based on wavefront measurements, in accordance with some embodiments.

The displayed image, in one embodiment, can be used for the diagnosis of poor subjective acuity that is not due to refractive errors in the eye but instead is due to potential retinal issues. FIG. 2c shows an example of an eye that can only see 20/40 subjectively with the best corrected lenses. Residual wave aberration of the tested eye 261 and estimated retinal image 262 from the residual wave aberration are shown. Clearly, optics of the eye with a correction lens would allow the eye to see far better than 20/20 according to the retinal image 262. Thus, the eye's inability to see 20/20 is not due to the eye's optics, but due to retinal issues.

The displayed image, in another embodiment, can be used for the diagnosis of poor subjective acuity due to the eye's refractive errors. When the residual aberrations are significant due to cases such as keratoconus, aberrations that are responsible for poor vision can also be identified even though they are often not correctable by eyeglasses.

The displayed image, in yet another embodiment, can be used for feedback by an operator to the software module for the determination of the prescription cylinder power CYL_p. If the estimated acuity in the displayed image is below 20/20, the operator can provide feedback to the software module so that the magnitude of CYL_p can be increased until the estimated acuity in the displayed image reaches 20/20.

The displayed image, in still another embodiment, can be used for the promotion of high-definition (HD) vision beyond conventional 20/20 acuity. Both high-definition vision with complete correction of eye's astigmatism and standard vision for 20/20 acuity with reduced image distortion are obtained at the same time. In the present embodiments, the standard can be raised for vision correction beyond 20/20 if a patient is found to have no image distortion problems with the clearest vision possible such as acuity of 20/10 or 20/12 acuity. This will improve quality of vision for a majority of population. For people who may have image distortion problems with the clearest vision possible, the standard vision with acuity of 20/20 is readily available. Patients will make their judgement using the method 200.

Returning to the method 200 of FIG. 2a, once the prescription cylinder power (CYL_p) is determined in steps 220, in steps 230, 232, 234 and 236 a prescription spherical power (SPH_s) is determined through a subjective refraction involving subjective responses of the patient to a plurality of spherical powers. The subjective refraction is performed using a phoropter module having a plurality of spherical lenses and cylindrical lenses or having one or more electrically-controlled lenses that is/are capable of achieving different sphero-cylinder corrections. In one embodiment an initial cylinder correction is dialed into the phoropter in step 230 according to 1) the objective spherical power SPH_o from the aberrometer module in step 210, 2) the prescription cylinder power CYL_p from the software module in step 220, and 3) the objective cylinder axis AXIS_o according to the objective aberrometer module in step 210. The phoropter module, containing a plurality of spherical lenses and cylindrical lenses or having one or more electric controlled lenses that is/are capable of achieving different sphero-cylinder corrections, allows the patient to preview any sphero-cylindrical prescription. An acuity chart with optical distance of 3 meters to 5 meters is viewed by the patient through the phoropter module.

In the subjective refraction, the patient is presented with a plurality of SPH settings, using the objective spherical power SPH_o from the aberrometer module as a possible starting point as indicated in step 230 of FIG. 2. The operator—who may be, for example, an optician, an optometrist, or a technician—updates the spherical power by an amount δSPH in step 232 of the subjective refraction. The patient provides a subjective response on whether the spherical power (i.e., focus power) is optimized. If the spherical power is not optimized in step 234, the operator changes the setting of spherical power by a revised amount of spherical power adjustment δSPH in step 236. The step 232 of updating SPH_s, step 234 of checking if the spherical power is optimized, and step 236 of changing the spherical power adjustment δSPH are then repeated until the spherical power is optimized.

From the subjective refraction of steps 230, 232, 234 and 236 a new, optimized, subjective spherical power SPH_s is obtained so that the patient obtains the best subjective acuity at the lowest spherical power for myopic eyes under the prescription cylinder power.

In step 240, the method includes generating a prescription for an ophthalmic lens of the eyeglasses. In some embodiments, at least one prescription is generated. The generating of the prescription includes: 1) the subjective prescription spherical power SPH_s that is determined through the subjective refraction in steps 230-236, 2) the prescription cylinder power CYL_p that is determined by the software module in step 220, and 3) the objective cylinder axis AXIS_o (i.e., cylinder angle) that is determined from the objective measurement of wave aberration in step 210. Because humans have two eyes, the prescription process and method described for one eye can be applied to both left and right eyes. The final prescription will include a subjective prescription spherical power SPH_s, a prescription cylinder power CYL_p, and an objective cylinder axis AXIS_o for each eye.

In one embodiment, the method 200 further includes step 238 of determining a plurality of prescription spherical powers (SPH_s1, SPH_s2) through the subjective refraction process steps 230 through 236 with a phoropter, which involves subjective responses of the patient to a plurality of spherical powers. A first prescription spherical power (SPH_s1) in the plurality of prescription spherical powers is associated with the objective cylinder power CYL_o and the objective cylinder axis AXIS_o. A second prescription spherical power (SPH_s2) in the plurality of prescription spherical powers is associated with the prescription cylinder power CYL_p and the objective cylinder axis AXIS_o.

In yet another embodiment, the method 200 further includes step 245 of generating a plurality of prescriptions for eyeglasses, including at least 1) a first, high-definition prescription that specifies the subjective, first prescription spherical power SPH_s1, the objective cylinder power CYL_o and the objective cylinder axis AXIS_o for the best image quality, and 2) a second prescription that specifies the subjective, second prescription spherical power SPH_s2, the prescription cylinder power CYL_p and the objective cylinder axis AXIS_o for 20/20 acuity and reduced image distortion. The first prescription can be classified as the high-definition prescription for obtaining the clearest vision possible, which will allow people to see much better than the normal 20/20 standard for high-definition vision. The second prescription can be classified as the standard 20/20 visual acuity prescription but having the unique feature of balancing retinal image quality and image distortion.

Operators can assemble a few trial lenses to let patients preview the high-definition prescription. If a patient has no issue in image distortion and lens adoption with the high-definition prescription, the patient should be offered with the high-definition eyeglasses that offers the best vision possible. On the other hand, if a patient has issues in image distortion and lens adoption with the high-definition prescription, the patient should be offered the standard eyeglasses that offers reduced image quality and reduced image distortion.

Figure 3:
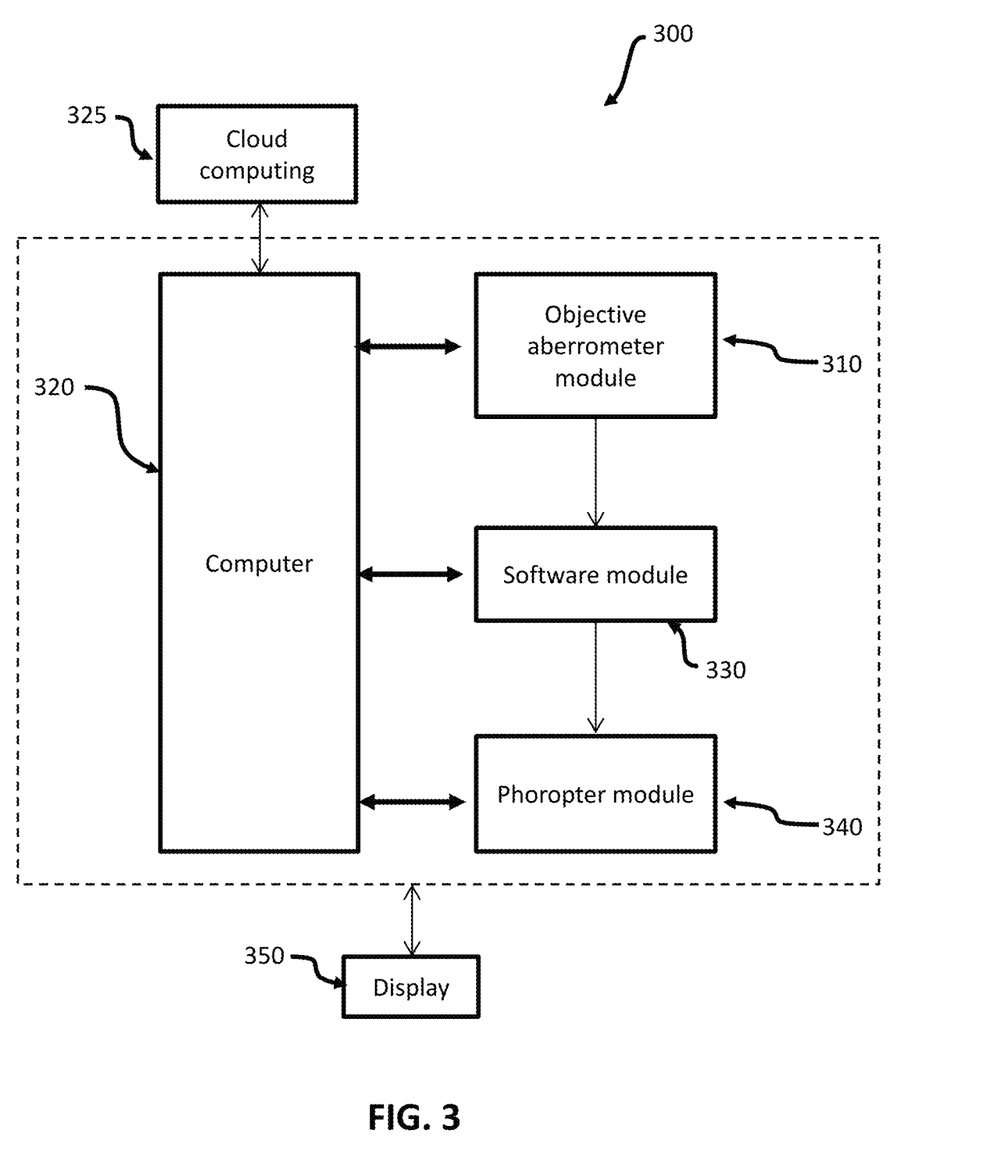
FIG. 3 shows a block diagram of an automated refraction system, in accordance with some embodiments.

FIG. 3 is a block diagram of a system 300 for determining refractive corrections for eyeglasses, in accordance with some embodiments. System 300 includes an objective aberrometer module 310 configured to obtain an objective measurement of a wave aberration of an eye of a patient. In one embodiment the objective aberrometer module includes 1) a wavefront sensor for measuring a wavefront, and 2) an optical relay for reproducing the wavefront from the eye to the wavefront sensor. A computer 320 is connected to the aberrometer module hardware 310 for processing the data from the wavefront sensor and generating wave aberration of a tested eye. The objective wavefront measurement includes all aberrations in the eye such as focus error, astigmatism, coma and spherical aberration. Computer 320 can be any electronic processor that is capable of receiving, storing, and calculating data. In some embodiments, the aberrometer and the phoropter form one system and the computer 320 processes information for both the aberrometer and the phoropter.

In some embodiments, the objective aberrometer module 310 uses a principle or device including but not limited to a Hartmann-shack sensor, laser ray tracing, spatially resolved refractometer, Talbot-Moire interferometry, skiascopic phase difference, Tscherning principle, and the like.

From the wave aberration, an objective correction is determined that provides the best retinal image possible. The objective correction includes an objective spherical power (SPH_o), an objective cylinder power (CYL_o) and an objective cylinder axis (AXIS_o). The objective correction is determined objectively, and it does not involve responses from a patient. The cylinder power is measured by the objective aberrometer module in an increment finer than 0.25 D. Because objective aberrometers are very precise, the objective cylinder power is typically in an increment of 0.01 D.

The objective correction are determined from the wave aberration through objective vision optimization to achieve a best image quality possible for the eye (i.e., sharpest vision, such as 20/10 acuity). In one embodiment, the objective aberrometer module is configured to determine the objective corrections of SPH_o, CYL_o, and AXIS_o by minimizing the residual RMS (Root Mean Square) wavefront error from the objective measurement of a wave aberration of an eye of a patient (W(x,y)).

In another embodiment, the objective corrections of SPH_o, CYL_o, and AXIS_o are determined through objective vision optimization to achieve a best image quality for the eye. This can be achieved by 1) numerically varying SPH_o, CYL_o, and AXIS_o in a plurality of combinations, 2) calculating retinal image quality objectively for each of the combinations, and 3) determining one combination of SPH_o, CYL_o, and AXIS_o with their corrections to achieve the best objective retinal image quality.

In one embodiment, objective retinal image quality is measured by one or more of the following parameters: Strehl ratio (peak intensity) of a point-spread function, or the half-height width of a point-spread function, or a modulation transfer function at certain spatial frequencies such as 30 cycles/deg (fundamental frequency for 20/20), 60 cycles/deg (fundamental frequency for 20/20), or variations of these frequencies.

In yet another embodiment, the system includes a cloud computing system 325 that is in communication with the computer 320 and that is configured to perform the objective vision optimization. The objective corrections of SPH_o, CYL_o, and AXIS_o are determined through objective vision optimization that is performed through the cloud computing.

System 300 also includes a software module 330 for determining a prescription cylinder power CYL_p. The software module 330 in one embodiment is configured as a software routine in computer 320 or in a cloud computing device, which process data according to the software module 330. The software module 330 uses the objective measurements from the objective aberrometer module 310 to determine the prescription power CYL_p. The absolute value of the prescription cylinder power (CYL_p) is less than an absolute value of the objective cylinder power (CYL_o) for reduced image distortion, but is large enough for achieving an acuity of at least 20/20. In other words, the software module may choose a cylinder power for the prescription that is less than what is needed to achieve a best vision condition (e.g., 20/10) while still ensuring that the corrected eye will achieve an acuity of at least 20/20. For example, the absolute value of the prescription cylinder power (CYL_p) ranges between the objective cylinder power (CYL_o) rounded down to a nearest 0.25 D, and the objective cylinder power reduced (CYL_o) by 0.75 D in absolute value. The exact amount of δCYL will differ from eye to eye. The resulting prescription cylinder power is CYL_p=CYL_o−δCYL. In other words, the prescription cylinder power can be up to 0.75 D less than the absolute value of the objective cylinder power, or can remain as much as the closest, lower 0.25 D increment of the objective cylinder power.

In one embodiment, the reduction from the objective cylinder power (CYL_o) to the prescription cylinder power (CYL_p) is determined by calculating the retinal image for varying values of cylinder powers including (CYL_o), using the same cylinder angle (AXIS_o). Visual acuity with the prescription cylinder power (CYL_p) and the objective cylinder axis (AXIS_o) is targeted at 20/20 from the calculated retinal images. Because the prescription cylinder power (CYL_p) is less than the CYL_o, the image distortion caused with the prescription cylinder power (CYL_p) will be reduced.

In yet another embodiment, the system includes a cloud computing system 325 as well as communication devices, which is configured to perform the objective vision optimization as well as the tasks in the software module.

In yet another embodiment, the method 200 includes presenting the calculated retinal images for two cylinder corrections—the cylinder powers of CYL_o and CYL_p with the same cylinder axis of AXIS_o—on a display 350. The display 350 may be, for example, a computer screen or other viewing monitor that is either physically incorporated with or is a separate component from the wavefront measurement aberrometer (i.e., objective aberrometer module 310) and/or phoropter module 340. In some embodiments as shown in the embodiment of FIG. 3, the objective aberrometer module 310 and phoropter module 340 are incorporated together into one physical system, where the computer 320 provides the computing capabilities for both the objective aberrometer module 310 and the phoropter module 340. In the embodiment of FIG. 3, the display 350 is connected to the unitary system that includes objective aberrometer module 310, computer 320, software module 330 and phoropter module 340.

The displayed calculated retinal images, in some embodiments, can be used for at least one of the following: i) diagnosis of poor subjective acuity that is due to potential retinal issues instead of refractive errors in the eye, ii) diagnosis of poor subjective acuity that is due to refractive errors, iii) feedback by an operator to the software module for the determination of the prescription cylinder power CYL_p, iv) high-definition vision beyond conventional 20/20 acuity.

System 300 further includes a phoropter module 340 for determining at least a prescription spherical power (SPH_s) through a subjective refraction. The phoropter module 340 can be, for example, a phoropter as described in Liang, U.S. Pat. No. 8,419,185, entitled "Methods and Devices for Refractive Correction of Eyes" which is fully incorporated by reference herein.

The software module 330 provides the prescription power CYL_p to the phoropter module 340. The phoropter module has a plurality of spherical lenses and cylindrical lenses or has one or more electrically-controlled lenses that is/are capable of achieving different sphero-cylinder corrections. The phoropter module is used for determining a prescription spherical power of the eye through subjective refraction, the subjective refraction involving subjective responses of the patient to a plurality of spherical powers. The phoropter module 340 is configured to dial in, to the cylindrical lenses: 1) the objective spherical power SPH_o, 2) a cylinder correction according to the prescription cylinder power CYL_p from the software module 330, and 3) the objective cylinder axis AXIS_o according to the objective aberrometer module. The phoropter module 340 allows a patient to preview any sphero-cylindrical prescription. Viewing an acuity chart through the phoropter 340 with optical distance of 3 meters to 5 meters away from a patient, the patient is presented with a plurality of spherical settings that use the objective spherical power SPH_o as a starting point in one embodiment. A new subjective sphere power SPH_s=SPH_o+δSPH is obtained so that the patient obtains the best subjective acuity under CYL_p at the lowest sphere power for myopic eyes. For eyes with hypopia, the operator determines the best subjective acuity for the tested patient at the highest sphere power.

From the subjective refraction performed using the phoropter module 340, at least one prescription is generated for one of an ophthalmic lens. The prescription includes: 1) the prescription subjective spherical power SPH_s that is determined subjectively through the subjective refraction using photopter module 340, 2) the prescription cylinder power CYL_p that is determined by the software module 330, and 3) the objective cylinder axis AXIS_o that is determined from the objective measurement of wave aberration by objective aberrometer module 310.

The present methods and systems as illustrated in FIGS. 2a-2c and 3 and described herein have many benefits. First, subjective refraction for cylinder power and cylinder in the conventional method of FIG. 1 is eliminated, and replaced with an objective wavefront measurement plus an objective optimization. The objective optimization is more precise and faster by being performed with computers as in the present embodiments, because computers enable checking every possible combination of SPH, CYL, AXIS for achieving the best corrected vision possible. By doing so, finding the prescription for eyeglasses for the best vision possible becomes faster, more accurate, and can be delegated to technicians.

Second, issues with adoption of new eyeglasses is handled by finding the prescription with reduced cylinder power CYL_p that still offers 20/20 acuity. In doing so, forcing patients to adapt to a new pair of eyeglasses with the best vision or remaking the new eyeglasses if the patient cannot get used to a new pair of eyeglasses will be eliminated.

Third, both high-definition vision with complete correction of eye's astigmatism and standard vision for 20/20 acuity with reduced image distortion are obtained at the same time. By doing so, the present embodiments raise the standard for vision correction beyond 20/20 if a patient is found to have no problem with clearest vision possible for 20/10 or 20/12 acuity, which will improve quality of vision for a majority of the population. For people who may have problems with the clearest vision possible (better than 20/20, e.g. 20/12 or 20/10), the standard vision with acuity of 20/20 is readily available. Patient will make their judgement with help of the method 200 and the system 300.

In summary, conventional refraction for eyeglasses relies on "human intelligence" for vision optimization, setting the targeted acuity based on experience and prescription adjustment if patients complain about their pairs of new eyeglasses. The methods in the present embodiments are revolutionary because all "human intelligence" for eye refraction is replaced by "machine intelligence" equipped with science and technologies for refraction automation. Also, the present embodiments resolve the conflict between having the best vision possible and having comfortable eyeglasses, and offers high-definition beyond traditional 20/20. The present embodiments furthermore enable vision diagnosis by separating causes of poor vision below 20/20 acuity from refractive errors or non-refractive errors.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A system for determining a refractive correction for eyeglasses, comprising:
an objective aberrometer module configured to obtain an objective measurement of a wave aberration of an eye of a patient, wherein the objective measurement includes an objective spherical power (SPH_o), an objective cylinder power (CYL_o), an objective cylinder axis (AXIS_o), and residual aberrations, wherein the objective measurement does not involve responses from the patient, and wherein the objective measurement uses objective vision optimization to achieve a best image quality for the eye;
a software module that is configured to determine a prescription cylinder power (CYL_p), wherein an absolute value of the prescription cylinder power is less than an absolute value of the objective cylinder power (CYL_o) and achieves an acuity of at least 20/20;
a phoropter module having 1) a plurality of spherical lenses and cylindrical lenses or 2) one or more electrically-controlled lenses that are capable of achieving different sphero-cylinder corrections, wherein the phoropter module is used for determining a prescription spherical power of the eye through a subjective refraction involving subjective responses of the patient to a plurality of spherical powers, wherein the phoropter module is configured to dial in, to the cylindrical lenses: i) a cylinder correction according to the prescription cylinder power (CYL_p) from the software module, and ii) the objective cylinder axis (AXIS_o) according to the objective aberrometer module; and
wherein a prescription for an ophthalmic lens of the eyeglasses includes: a) the prescription spherical power (SPH_s) that is determined through the subjective refraction, b) the prescription cylinder power (CYL_p) that is determined by the software module, and c) the objective cylinder axis (AXIS_o) that is determined from the objective measurement of the wave aberration;
wherein:
the absolute value of the prescription cylinder power (CYL_p) ranges between the objective cylinder power (CYL_o) rounded down to a nearest 0.25D, and the objective cylinder power (CYL_o) reduced by 0.75D in absolute value;
the reduction from the objective cylinder power (CYL_o) to the prescription cylinder power (CYL_p) is determined by calculating retinal images for a plurality of cylinder power values including (CYL_o) under the objective cylinder axis (AXIS_o);
a visual acuity under the prescription cylinder power (CYL_p) and the objective cylinder axis (AXIS_o) is estimated to be 20/20 or better from the calculated retinal images; and
the prescription cylinder power (CYL_p) is less than the CYL_o so that image distortion caused by the prescription cylinder power is reduced.

2. The system of claim 1, wherein the objective aberrometer module comprises a principle or device chosen from the group consisting of: a Hartmann-shack sensor, laser ray tracing, a spatially resolved refractometer, Talbot-Moire interferometry, skiascopic phase difference, and Tscherning principle.

3. The system of claim 1, wherein the objective aberrometer module is configured to determine the SPH_o, the CYL_o, and the AXIS_o by minimizing a residual RMS (Root Mean Square) wavefront error from the objective measurement of the wave aberration.

4. The system of claim 1, wherein the objective vision optimization to achieve the best image quality for the eye comprises:
numerically varying SPH_o, CYL_o, and AXIS_o in a plurality of combinations;
calculating a retinal image quality objectively for each combination in the plurality of combinations; and
determining a combination of SPH_o, CYL_o, and AXIS_o to achieve the best image quality, wherein objective retinal image quality is measured by one or more of: a Strehl ratio of a point-spread function, a half-height width of a point-spread function, a modulation transfer function at a spatial frequency.

5. The system of claim 4, further comprising a cloud computing system that is in communication with the objective aberrometer module and that is configured to perform the objective vision optimization and tasks in the software module.

6. The system of claim 1, further comprising a display that is configured to display the calculated retinal images for a) CYL_o with AXIS_o for the best image quality, and b) CYL_p with AXIS_o for balanced vision retinal image quality and reduced image distortion;
wherein the displayed calculated retinal images are for at least one of the following: i) diagnosis of poor subjective acuity that is due to potential retinal issues instead of refractive errors in the eye, ii) diagnosis of poor subjective acuity that is due to refractive errors, iii) feedback by an operator to the software module for the determining of the prescription cylinder power CYL_p, iv) high-definition vision beyond conventional 20/20 acuity.

7. The system of claim 1, wherein the subjective refraction comprises determining a plurality of prescription spherical powers (SPH_s1, SPH_s2), wherein a first prescription spherical power (SPH_s1) is associated with the objective cylinder power CYL_o and the objective cylinder axis AXIS_o and a second prescription spherical power (SPH_s2) is associated with the prescription cylinder power CYL_p and the objective cylinder axis AXIS_o.

8. The system of claim 7, wherein a plurality of prescriptions for the eyeglasses is generated, including 1) a high-definition prescription that specifies the first prescription spherical power SPH_s1, the objective cylinder power CYL_o and the objective cylinder axis AXIS_o for the best image quality, and 2) a prescription that specifies the second prescription spherical power SPH_s2, the prescription cylinder power CYL_p and the objective cylinder axis AXIS_o for 20/20 acuity and reduced image distortion.

* * * * *